US00PP26748P3

(12) United States Plant Patent
Caster et al.

(10) Patent No.: US PP26,748 P3
(45) Date of Patent: May 24, 2016

(54) BLUEBERRY PLANT NAMED 'DRISBLUETWELVE'

(50) Latin Name: ***Vaccinium corymbosum* L.**
Varietal Denomination: DrisBlueTwelve

(71) Applicant: DRISCOLL STRAWBERRY ASSOCIATES, INC., Watsonville, CA (US)

(72) Inventors: Brian K. Caster, Salinas, CA (US); Arlen Draper, Payson, AZ (US); Jennifer K. Izzo, Watsonville, CA (US); Jorge Rodriguez Alcazar, Texcoco (MX)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 169 days.

(21) Appl. No.: 13/998,800

(22) Filed: Dec. 9, 2013

(65) Prior Publication Data

US 2015/0163971 P1 Jun. 11, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Jondle & Associates, P.C.

(57) ABSTRACT

A new and distinct variety of blueberry plant named 'DrisBlueTwelve' particularly distinguished by having a late harvest season, very low chilling requirement and sweet berries with very low acidity, is disclosed.

2 Drawing Sheets

Genus and species: *Vaccinium corymbosum* L.
Variety denomination: 'DrisBlueTwelve'.

BACKGROUND OF THE NEW PLANT

The invention relates to a new and distinct blueberry variety designated 'DrisBlueTwelve' and botanically known as *Vaccinium corymbosum* L. This new blueberry variety was discovered in Santa Cruz County, Calif. in August 2004 and originated from a cross between the female parent blueberry plant 'Jewel' (U.S. Plant Pat. No. 11,807) and the proprietary male parent blueberry plant 'FL 95-54' (unpatented). The original seedling of the new variety was first asexually propagated via softwood cuttings at a nursery in Monterey County, Calif. in 2004. 'DrisBlueTwelve' was subsequently asexually propagated via softwood cuttings and underwent further testing at a nursery in Guzmán, Mexico for five years (2009-2013). The present invention has been found to be stable and reproduce true to type through successive asexual propagations via softwood cuttings.

Plant Breeder's Rights for this variety have not been applied for. 'DrisBlueTwelve' has not been made publicly available or sold more than one year prior to the filing date of this application.

SUMMARY OF THE INVENTION

The following are the most outstanding and distinguishing characteristics of this new cultivar when grown under normal horticultural practices in Guzmán, Mexico.

1. Late harvest season;
2. Very low chilling requirement; and
3. Sweet berries with very low acidity.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are six years old.

DESCRIPTION OF THE NEW CULTIVAR

Figure 1:
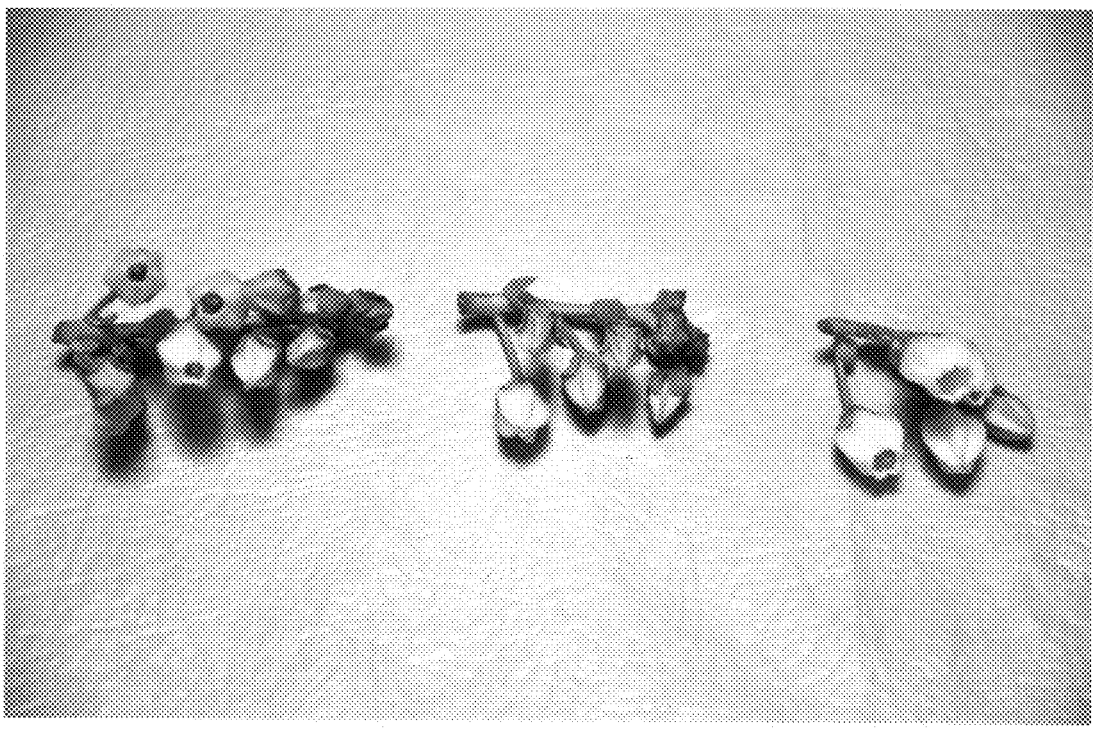
FIG. 1 shows a close-up of flower buds and mature flowers.
Figure 2:
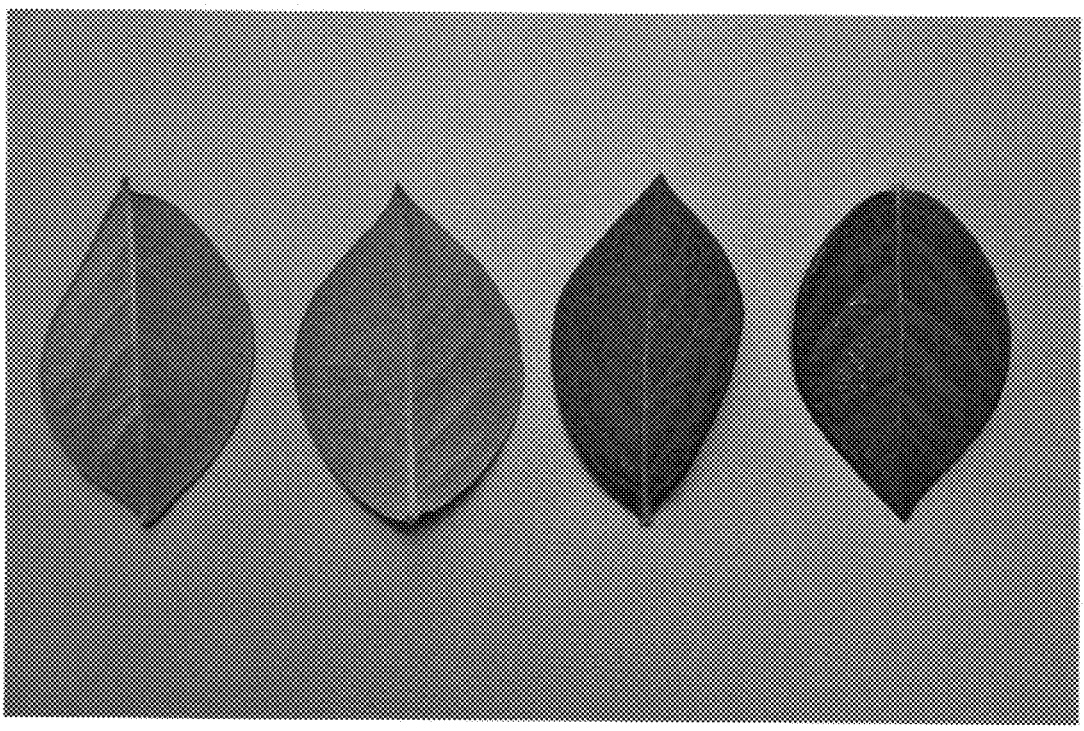
FIG. 2 shows a close-up of the leaves.
Figure 3:
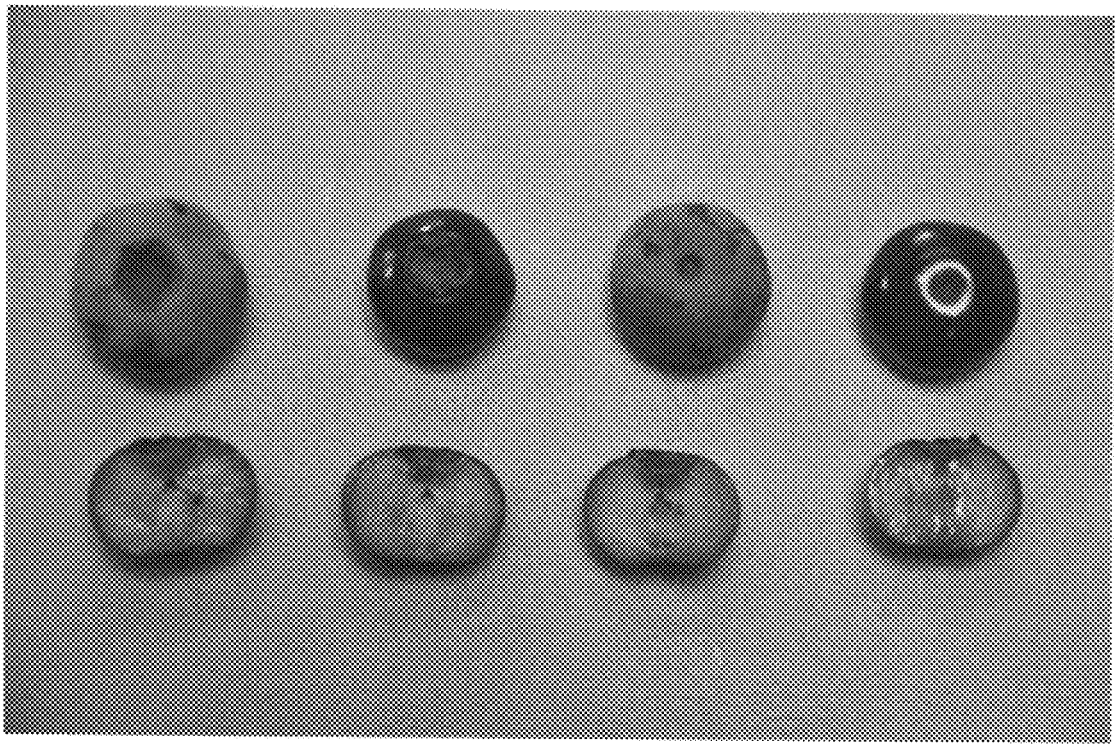
FIG. 3 shows a close-up of the whole fruit and a cross-section of the fruit.

The following detailed description sets forth the distinctive characteristics of 'DrisBlueTwelve.' The data which define these characteristics is based on observations taken in Guzmán, Mexico from 2009-2013. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwelve' has not been observed under all possible environmental conditions. The botanical description of 'DrisBlueTwelve' was taken from 6 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueTwelve'.

Parentage:

*Female parent*.—The blueberry plant 'Jewel' (U.S. Plant Pat. No. 11,807).

*Male parent*.—The proprietary blueberry plant 'FL 95-54' (unpatented).

Plant:

*Size*.—Very large.

*Height*.—183.7 cm.

*Width*.—182.0 cm.

*Length/width ratio*.—1.0.

*Plant vigor*.—Strong.

*Growth habit*.—Upright.

*Productivity*.—High.

*Cold hardiness*.—Medium; USDA Plant Hardiness Zone 9.

*Chilling requirement*.—Very low; 100-200 chilling hours.

*Propagation*.—Soft wood cuttings.

*Time of vegetative bud burst*.—Early.

*Fruiting type*.—Only on one-year-old shoots.

*Cane renewal*.—Strong.

*Internode length* (*upper half on one-year old shoot*).—47.2 mm.

*One-year old canes* (*young canes*).—Length: 114.6 cm. Diameter at the base: 76.0 mm. Diameter at the tip: 10.6 mm. Texture: Rough. Color (One-year old shoot, branch and canes): RHS 183B (Dark greyed-purple).

*Five-year old canes* (*mature canes*).—Length: 180.8 cm. Diameter at the base: 32.3 mm. Diameter at the tip: 28.1 mm. Texture: Rough. Color: RHS 199D (Light greyed-brown).

Leaves:

*Length*.—Medium; 8.02 cm.

*Width*.—Medium; 4.52 cm.

*Length/width ratio*.—1.8; Longer than broad.

*Appearance of leaf bud*.—Early.

*Shape*.—Elliptic.

*Apex*.—Acute.

*Base*.—Cuneate.

*Margin*.—Entire.

*Glossiness*.—Glossy.

*Pubescence*.—Glabrous (Absent).

*Sheath*.—Absent.

*Arrangement*.—Alternate.

*Venation*.—Reticulate.

*Color*.—Upper surface: Dark; RHS 137A (Dark green). Lower surface: Medium; RHS 138B (Medium green).

*Internode length* (*one-year old shoot, upper half*).—Medium; 64.15 mm.

Petiole:

*Length*.—4.0 mm.

*Diameter*.—2.65 mm.

*Color*.—RHS 144D (Light yellow-green).

Flowers:

*Length* (*excluding peduncle*).—Medium; 11.05 mm.

*Diameter*.—7.80 mm.

*Length/width ratio*.—1.4.

*Color*.—RHS 155B (White).

*Flower bud*.—Length: 3.72 mm. Width: 7.21 mm. Number of flowers per bud: 4. Anthocyanin coloration: Strong; RHS 60A (Dark red-purple). Color on immature buds: Light; RHS 145B (Light yellow-green). Color on mature buds: Medium; RHS 145A (Medium yellow-green).

*Petal width*.—9.80 mm.

*Fragrance*.—Very faint or absent.

*Time of beginning flowering on one-year shoot*.—Medium.

*Time of flowering* (50% *antithesis or full bloom*).—Medium.

*Flowering interval*.—January.

*Pedicel*.—Length: 4.49 mm. Diameter: 1.00 mm. Color: RHS 144B (Medium yellow-green).

*Corolla*.—Diameter of corolla tube: 7.8 mm. Height of corolla tube: 11.5 mm. Aperture diameter: 5.65 mm. Shape: Urceolate (Urn-shaped). Size of corolla tube: Medium. Ridges on tube: Present.

*Peduncle*.—Length: 44.00 mm. Surface texture: Smooth. Color: RHS 144B (Medium yellow-green).

Reproductive Organs:

*Style length* (*including stigma*).—Medium; 8.60 mm.

*Style color*.—RHS 144B (Medium yellow-green).

*Pollen amount*.—Very low.

*Pollen color*.—RHS 155D (White).

*Pollination requirement*.—Intermediate.

*Anther color*.—RHS 167B (Medium greyed-orange).

*Ovary color*.—RHS 55B (Light red).

Fruit:

*Size*.—Medium.

*Length*.—13.90 mm.

*Width*.—16.70 mm.

*Length/width ratio*.—0.8.

*Fruit pedicel diameter*.—4.49 mm.

*Weight*.—2.0 g.

*Number of berries per cluster*.—8.20.

*Cluster density*.—Medium.

*Shape in longitudinal sections*.—Oblate.

*Intensity of green color* (*immature fruit with bloom*).—Light; RHS 142C (Light green).

*Color of skin* (*immature fruit without bloom*).—RHS 178B (Dark greyed-red).

*Color of skin* (*mature fruit without bloom*).—RHS N186A (Dark greyed-purple).

*Color of skin* (*mature fruit with bloom*).—RHS 97B (Light violet-blue).

*Intensity of bloom* (*mature fruit*).—Strong.

*Attitude of sepals*.—Incurving.

*Calyx*.—Diameter of basin: Very small; 6.70 mm. Depth of basin: Very shallow; 2.00 mm. Diameter/depth ratio: 3.4.

*Flesh color*.—RHS 154D (Light yellow-green).

*Firmness*.—Firm.

*Sweetness*.—High.

*Acidity*.—Very low.

*Time of beginning of fruit ripening* (*one-year old shoots*).—Late.

*Harvest season*.—Late.

*Harvest interval*.—February-June.

Seeds:

*Length*.—1.60 mm.

*Width*.—1.00 mm.

*Length/width ratio*.—1.6.

*Abundance*.—Very low.

*Color*.—RHS N167A (Medium greyed-orange).

Resistance to pests and diseases: Data not available.

COMPARISON WITH PARENTAL AND COMMERCIAL VARIETIES

'DrisBlueTwelve' differs from the female parent 'Jewel' (U.S. Plant Pat. No. 11,807) in that the fruit of 'DrisBlueTwelve' is sweeter, juicier, and more aromatic than 'Jewel'.

'DrisBlueTwelve' differs from the male parent 'FL 95-54' (unpatented) in that 'DrisBlueTwelve' is much more vigorous and makes a more bushy canopy than 'FL 95-54'. Additionally, the fruit of 'FL 95-54' are lighter blue in color due to more bloom than the fruit of 'DrisBlueTwelve'.

'DrisBlueTwelve' differs from the commercial variety 'DrisBlueFour' (U.S. application Ser. No. 13/573,345) in that 'DrisBlueTwelve' has later production in Mexico than 'DrisBlueFour'. Additionally, 'DrisBlueTwelve' has an upright growth habit, whereas 'DrisBlueFour' has a semi-erect growth habit.

We claim:

1. A new and distinct variety of blueberry plant named 'DrisBlueTwelve' as shown and described herein.

* * * * *